United States Patent [19]

Nyeki et al.

[11] 4,330,532

[45] May 18, 1982

[54] ANGIOTENSIN-II ANALOGUES WITH ANTAGONIZING EFFECTS, CONTAINING AN α-HYDROXYCARBOXYLIC ACID RESIDUE IN POSITION 8, AND A PROCESS FOR THE PREPARATION THEREOF

[75] Inventors: Olga Nyéki; Lajos Kisfaludy; Egon Kárpáti; László Szporny, all of Budapest, Hungary

[73] Assignee: Richter Gedeon Vegyeszeti Gyar Rt., Budapest, Hungary

[21] Appl. No.: 222,765

[22] Filed: Jan. 6, 1981

[30] Foreign Application Priority Data

Jan. 18, 1980 [HU] Hungary ................................ 100/80

[51] Int. Cl.³ ..................... A61K 37/00; C07C 103/52
[52] U.S. Cl. ................................ 424/177; 260/112.5 R
[58] Field of Search .................. 260/112.5 R; 424/177

[56] References Cited

U.S. PATENT DOCUMENTS

| | | | |
|---|---|---|---|
| 3,920,627 | 11/1975 | Wissmann et al. | 260/112.5 R |
| 3,947,575 | 3/1976 | Ondetti | 260/112.5 R |
| 3,975,365 | 8/1976 | Mazur | 260/112.5 R |
| 4,013,791 | 3/1977 | Wissmann et al. | 260/112.5 R |
| 4,179,433 | 12/1979 | Kisfaludy et al. | 260/112.5 R |
| 4,209,442 | 6/1980 | Kisfaludy et al. | 260/112.5 R |

*Primary Examiner*—Delbert R. Phillips
*Attorney, Agent, or Firm*—Karl F. Ross

[57] ABSTRACT

New angiotensin-II analogues of the general formula (I),

X-Arg-Val-Tyr-Ile-His-Pro-Y-OA    (I)

wherein

X stands for the acyl group of an N-methylamino acid, or the acyl group of an aliphatic α-aminooxy- or α-hydroxycarboxylic acid, Y is the residue of an aliphatic α-hydroxycarboxylic acid, and A is hydrogen or a $C_{1-5}$ alkyl group, are prepared by removing the protecting groups of a protected octapeptide derivative of the general formula (II) or (III), B-X-Arg(C)-Val-Tyr(D)-Ile-His(E)-Pro-Y-OF    (II)

B-X-Arg(C)-Val-Tyr(D)-Ile-His(E)-Pro-Y-OA    (III)

wherein

B is a group removable by acidolysis or catalytic hydrogenation,

C is a group for the temporary protection of the guanidino group on the Arg moiety, D is a group for the temporary protection of the aromatic hydroxy group on the Tyr moiety, E is a group for the temporary protection of the imidazole group on the His moiety, and F is a group for the protection of the terminal carboxy group, resistant to the effect of mild acids but removable by catalytic hydrogenolysis or upon treatment with a stronger acid.

The new compounds of the invention can be applied to diagnose and differentiate hypertensions of various origin, and in the therapy to suppress hypertensions of renal origin, in the treatment of hypertensive crises, secondary cardiac insufficiency, etc.

5 Claims, No Drawings

ANGIOTENSIN-II ANALOGUES WITH ANTAGONIZING EFFECTS, CONTAINING AN α-HYDROXYCARBOXYLIC ACID RESIDUE IN POSITION 8, AND A PROCESS FOR THE PREPARATION THEREOF

The invention relates to new peptides with angiotensin-II effects, to pharmaceutical compositions containing them, as well as to a process for the preparation thereof.

The new compounds according to the invention correspond to the formula $$\text{X-Arg-Val-Tyr-Ile-His-Pro-Y-OA} \qquad (I),$$

wherein
- X stands for the acyl group of an N-methylamino acid, preferably a sarcosyl group, or the acyl group of an aliphatic α-aminooxy- or α-hydroxycarboxylic acid,
- Y is the residue of an aliphatic α-hydroxycarboxylic acid, preferably a residue of lactic acid or L-2-hydroxy-3-methyl-valeric acid, and
- A is hydrogen or a $C_{1-5}$ alkyl group.

The acid addition salts and complexes of the above peptides are also embraced by the scope of the invention.

The first angiotensin-II analog, which proved to be a specific competitive inhibitor of angiotensin-II under both in vitro and invivo conditions, was described in 1970 [G. R. Marshal et al.: Proc. Natl. Acad. Sci. USA 67, 1624 (1970); P. A. Khairallah et al.: J. Med. Chem. 13, 181 (1970)]. This recognition initiated extensive research work for the production of angiotensin-II analog with antagonizing effects which may be used to diagnose certain renine-dependent hypertensions and in the treatment of such conditions as well. (Sar$^1$, Ala$^8$)-angiotensin-II, one of the many analogs with antagonizing effects prepared so far, has already been put on the market under the trade name Saralasin [D. T. Pals et. al.: Circ. Res. 29, 673 (1971)]. Clinical tests performed with this compound have shown that the substance is applicable for the diagnosis of hypertension of varying origin [G. Bönner et al/.: Dtsch. Med. Wschr. 104, 432 (1979)], as well as in the treatment of such conditions [J. L. Marx: Science 194, 821 (1976)]. More recently it has been found that substances with angiotensin-II antagonizing effects can be used in the treatment of cardiac insufficiencies caused by renovascular hypertension, too [H. Gavras et al.: JAMA 238, 880 (1977)].

By studying the relationships between the structures and biological effects of the angiotensin-II analogs prepared so far, several pieces of information have been obtained on the interpretation of agonistic and antagonistic effects. The main goal of recent research work has been to produce antagonistic substances with prolonged biological half life-times, which are free of certain undesired side effects, such as initial agonistic effects.

It has now been found that when replacing the phenylalanine moiety in position 8 of the angiotensin-II molecule by an aliphatic α-hydroxycarboxylic acid residue, and simultaneously introducing an N-methylamino acid, preferably sarcosine or an α-hydroxy- or α-aminooxycarboxylic acid moiety described by us before and proved to be effective for the same purpose (see German patent applictions Nos. 28 31 271 and 28 31 534), into position 1 of the molecule, new competitive inhibitors of angiotensin-II are obtained, which decrease the hypertension provoked by angiotensin-II under in vivo conditions considerably, and are active even upon subcutaneous administration.

The new compounds of the formula (I)

$$\text{X-Arg-Val-Tyr-Ile-His-Pro-Y-OA} \qquad (I)$$

are prepared according to the invention so that
(a) when a compound of the formula (I) in which
A is hydrogen is to be prepared, the protecting groups of a protected octapeptide derivative of the formula (II), $$\text{B-X-Arg(C)-Val-Tyr(D)-Ile-His(E)-Pro-Y-OF} \qquad (II)$$

wherein
- B is a group removable by acidolysis or catalytic hydrogenation, preferably a benzyloxycarbonyl or tert.-butoxycarbonyl group,
- C is a group for the temporary protection of the guanidino group on the Arg moiety, preferably a nitro or a tosyl group,
- D is a group for the temporary protection of the aromatic hydroxy group on the Tyr moiety, preferably a benzyl or a substituted benzyl group,
- E is a group for the temporary protection of the imidazole group on the His moiety, preferably a dinitrophenyl group, and
- F is a group for the protection of the terminal carboxy group, resistant to the effect of mild acids but removable by catalytic hydrogenolysis or upon treatment with a stronger acid, or (b) when a compound of the formula (I) in which A is a $C_{1-5}$ alkyl group is to be prepared, the protecting groups of a protected octapeptide of the formula (III), $$\text{B-X-Arg(C)-Val-Tyr(D)-Ile-His-(E)-Pro-Y-OA} \qquad (III)$$

wherein A, B, C, D and E are as defined above, are removed either stepwise or in a single step.

If desired, the resulting compounds of the formula (I) are converted into their acid addition salts or complexes.

The octapeptide derivatives of the formulae (II) and (III), used as starting substances in the process of the invention, can be prepared by any method known in peptide chemistry, e.g. as described in the Hungarian patent specification No. 168,431. When preparing the protected octapeptides, protecting groups which are stable under the conditions of acidolysis used to remove the N-terminal protecting group after the coupling reaction should be utilized to protect the functional side groups.

According to a preferred method of the invention, the protected octapeptide derivatives of the formulae (II) and (III) are built up stepwise, and groups which can be removed easily by acidolysis, e.g. tert.-butoxycarbonyl group, are used to protect temporarily the terminal amino groups of the individual amino acid derivatives. The protecting groups attached to the starting octapeptide derivative are split off preferably in a single step by catalytic hydrogenolysis, after removing the dinitrophenyl group by thiolysis.

The α-hydroxycarboxylic acid residue is introduced into position 8 of the molecule preferably so that an esterified α-hydroxycarboxylic acid of the formula (IV),

wherein Y is as defined above and Z is an alkyl or an aralkyl group, is reacted with an N-protected proline, the protecting group being preferably a tert.-butoxycarbonyl group. The —CO—O— bond formed in this reaction is stable and does not split in the subsequent steps of the synthesis.

The compounds of the formula (I) are purified by methods known per se, preferably by ion exchange chromatography on carboxymethyl cellulose. The endproduct is separated from the effluent preferably by freeze-drying, to obtain a powdery substance which can be used directly in the preparation of various pharmaceutical compositions.

The antagonistic effects of the new compounds of the formula (I) were investigated on narcotized male cats. After treating the animals with a ganglion blocking agent and bisecting the cervical vagus nerves on both sides, the animals were treated with an infusion of Hypertensin (CIBA) at a rate of 0.5 μg/kg/min. When the blood pressure of the animals reached a steady, increased level, the substance to be tested was administered either intravenously or subcutaneously in physiological saline solution or as an aqueous solution which also contained a carrier. The blood pressure drop was measured in mm Hg units, and the extent of decrease was expressed in percents related to the value before treatment. The statistical evaluation was performed on the basis of the blood pressure differences, by Student's single sample "t" test. The results are summarized in Table 1. The term "duration of effect" denotes the period elapsed until the observation of the last still significant (p±5%) blood pressure difference.

types, carboxymethyl cellulose, alginates, polyflorethine-phosphates, amino acid polymers and copolymers, etc. are to be mentioned. As mineral complexing agents. e.g. zinc hydroxide and low solubility zinc salts, such as zinc phosphates, can be used.

The new peptides according to the invention, furthermore their pharmaceutically acceptable salts and complexes can be used in therapy in the form of conventional pharmaceutical compositions. These compositions contain the new compounds according to the invention in admixture with an organic or mineral carrier applicable for enteral or parenteral administration. The pharmaceutical compositions may be e.g. freeze-dried solids containing carriers which do not react with the peptide, such as carbohydrates, furthermore concentrated or dilute suspensions and emulsions which may also contain various preservatives and stabilizers.

The pharmaceutical compositions can be used to diagnose and differentiate hypertension of different origins, and in therapy to suppress hypertension of renal origin, in the treatment of hypertensive crises, secondary cardiac insufficiency, etc.

The pharmaceutical compositions are presented preferably in the form of injections containing 1 to 10 mg of active agent. The active agents according to the invention can be used in daily doses of 1 to 10 mg for the treatment of adults. This amount is introduced preferably once a day in the form of an intravenous, subcutaneous or intramuscular injection or as a slow intravenous infusion.

The invention is elucidated in detail by the aid of the following non-limiting Examples.

The abbreviations used in the examples correspond to those generally applied in the literature [J. Biol. Chem. 247, 977 (1972)]. Further abbreviations are: Lac=L-lactic acid, HMV=L-2-hydroxy-3-methylvaleric acid, Pfp=pentafluorophenyl.

TABLE 1

Hypotensive effects of angiotensin-II analogs containing an α-hydroxycarboxylic acid residue in position 8

| Analogs | i.v. | | | | s.c., phys.sal. | | | | s.c., CMC | | | | s.c., gelatine | | | |
|---|---|---|---|---|---|---|---|---|---|---|---|---|---|---|---|---|
| | d | n | % | p | d | n | % | p | d | n | % | p | d | n | % | p |
| (Sar$^1$,L-Lac$^8$)Ang-II | 10 | 5 | 23 | 15 | 50 | 5 | 29 | 90 | 50 | 6 | 25 | 45 | 50 | 5 | 24 | 90 |
| | 20 | 5 | 29 | 15 | 100 | 5 | 33 | 120 | 100 | 6 | 27 | 90 | 100 | 5 | 32 | 90 |
| | | | | | 200 | 5 | 47 | 180 | 200 | 5 | 22 | 45 | 200 | 5 | 28 | 120 |
| (Sar$^1$,L-Lac—OEt$^8$)Ang-II | 10 | 5 | 27 | 12 | 100 | 6 | 15 | 45 | 100 | 5 | 41 | 90 | | | | |
| | 20 | 8 | 40 | 25 | | | | | | | | | | | | |
| (Sar$^1$,HMV$^8$)Ang-II | 10 | 5 | 33 | 45 | 100 | 5 | 18 | 30 | 100 | 5 | 35 | 300 | | | | |
| | 20 | 6 | 40 | 20 | | | | | | | | | | | | |
| Saralasin | 10 | 5 | 32 | 15 | 100 | 6 | 29 | 60 | 100 | 5 | 23 | 45 | 200 | 4 | 23 | φ |
| | | | | | 200 | 5 | 24 | 45 | 200 | 7 | 28 | 90 | | | | |

Remarks to Table 1:
d = dose, μg/kg
n = number of tests
p = duration of effect, minutes
phys. sal. = physiological saline solution
CMC = carboxymethyl cellulose From the data of Table 1 it can be seen that all of the angiotensin-II analogs which contain an α-hydroxycarboxylic acid residue in position 8 and a sarcosyl group in position 1 possess significant hypotensive effects. This effect is significant even upon subcutaneous administration; when the compounds are administered in a solution which also contains a carrier, the duration of the effect may sometimes reach several hours.

The term "pharmaceutically acceptable complex" denotes compounds of the peptides of the formula (I) formed with certain organic or mineral substances which provide a protracted effect for the active agent. Of the organic complexing agents, e.g. certain gelatine When preparing the compounds, evaporation was always performed on a Büchi-type Rotavapor apparatus. The thin layer chromatograms were taken on a "Kieselgel-6" silica gel layer prepared according to Stahl, and the following solvent mixtures were applied to develop the chromatograms:

(1) n-hexane:ethyl acetate=4:1
(2) ethyl acetate: (pyridine:acetic acid:water=20:6:11)=95:5
(3) ethyl acetate: (pyridine:acetic acid:water=20:6:11)=90:10

(4) ethyl acetate: (pyridine:acetic acid:-water=20:6:11)32 80:20
(5) ethyl acetate: (pyridine:acetic acid:-water=20:6:11)=70:30
(6) n-butanol:acetic acid:water 4:1:5 (upper phase)
(7) n-butanol:acetic acid:pyridine:water=30:6:20:24
(8) n-butanol:ethyl acetate:acetic acid:water=1:1:1:1

The thin layer chromatograms were visualized with ninhydrine or with chlorotolidine-potassium iodide.

The following general method was used to purify the end-products:

0.5 g of the free peptide are dissolved in 4 ml of a 0.01 molar ammonium acetate solution, and the solution is layered onto a column of 0.5 liters of carboxymethyl cellulose (CMC-52) equilibrated previously with the same buffer solution. A gradient mixture of 1.5 liters of a 0.01 molar ammonium acetate solution and 1.5 liters of a 0.4 molar ammonium acetate solution is applied as eluting agent. The eluting agent is passed through the column at a rate of 25 ml/hour, and the effluent is collected into fractions of 10 ml each. The composition of the effluent leaving the column is monitored continuously by an LKB Uvicord-II apparatus, the main fraction is separated on the basis of the curved obtained, and then freeze-dried in a Leybold-Hereus freeze-drier. If necessary, the product is subjected repeatedly to chromatography, by applying gradient elution again.

EXAMPLE 1

Preparation of (sarcosine[1],L-lactic acid[8])-angiotensin-II

Step 1

Preparation of Boc-Pro-Lac-OBzl 2.4 g (15 mmoles) of carbonyldiimidazole are added at 0° C., within 10 minutes, to a stirred solution of 2.15 g (10 mmoles) of Boc-Pro-OH in 10 ml of dry tetrahydrofuran. Thereafter a solution of 1.8 g (10 mmoles) of benzyl L-lactate in 10 ml of dry tetrahydrofuran, cooled to 0° C., is added dropwise to the reaction mixture at 0° C. within 15 minutes. The resulting mixture is stirred at 0° C. for 30 minutes and then at 20° C. for 2 hours; thereafter the mixture is stored in a refrigerator. Next day the solvent is removed, the residue is dissolved in 30 ml of chloroform, and the solution is washed successively with 1 n hydrochloric acid (4×10 ml), water, aqueous sodium hydrocarbonate solution (2×15 ml) and then with water again. The chloroform solution is dried and evaporated until constant weight. The oily residue is dried in a desiccator over phosphorous pentoxide to obtain 3.0 g (80%) of Boc-Pro-Lac-OBzl, a chromatographically uniform product; $R_f^{(1)}=0.32$, $R_f^{(2)}=0.57$.

Step 2

Preparation of Z-Sar-Arg(NO$_2$)-Val-Tyr(Bzl)-Ile-His(Dnp)-Pro-Lac-OBzl

A solution of 2.85 g (7.5 mmoles) of Boc-Pro-Lac-OBzl in 15 ml of a 8 n hydrochloric acid solution in dioxane is allowed to stand for 15 minutes. 30 ml of dry ether are added to the solution, and the mixture is evaporated to dryness. The resulting free dipeptolide hydrochloride, $R_f^{(5)}=0.37$, is dissolved in 20 ml of dimethyl formamide, the pH of the solution is adjusted to 8 with triethyl amine, and then 2.9 g (5 mmoles) of Boc-His(Dnp)-OPfp are added. The reaction mixture is stirred for one hour, and the pH of the mixture is maintained at 8. Thereafter the solvent is evaporated, the residue is dissolved in ethyl acetate, and this solution is washed successively with 10% aqueous citric acid solution, 1 n aqueous hydrochloric acid, 5% aqueous sodium hydrocarbonate solution and then with water. The solution is dried, the solvent is removed, and the resulting crude protected tripeptide, $R_f^{(2)}=0.77$, is dissolved in 10 ml of a 8 n hydrochloric acid solution in dioxane. After 20 minutes of standing the free tripeptide hydrochloride is precipitated with dry ether, the solid is filtered off and washed with ether. The resulting free tripeptide hydrochloride, $R_f^{(4)}=0.10$, is dissolved in 20 ml of dimethyl formamide, the pH of the solution is adjusted to 8 with triethyl amine, and 2.78 g (7.5 mmoles) of Boc-Ile-OPfp are added to the mixture. The reaction mixture is stirred for one hour, and the pH of the mixture is maintained at the initial value. Thereafter the solvent is evaporated, the residue is dissolved in ethyl acetate, and the solution is washed as described above. The solution is dried, the solvent is evaporated, the residue is triturated with n-hexane and the solid is filtered off. The resulting protected tetrapeptide, $R_f^{(2)}=0.67$, is dissolved in 10 ml of a 8 n hydrochloric acid solution in dioxane, the solution is allowed to stand for 15 minutes, and the free tetrapeptide hydrochloride, $R_f^{(5)}=0.52$, is precipitated with dry ether. This compound is dissolved in 20 ml of dimethyl formamide, the pH of the solution is adjusted to 8, 3.24 g (6 mmoles) of Boc-Tyr(Bzl)-OPfp are added, and the mixture is stirred for 30 minutes under maintaining the pH at the initial value. The solvent is removed, the residue is dissolved in ethyl acetate, and 0.22 ml of N,N-dimethylaminoethylamine are added to the mixture in order to remove the excess of the active ester. After 15 minutes of standing the solution is washed successively with 10% aqueous citric acid solution, 1 n aqueous hydrochloric acid, water, 5% aqueous sodium hydrocarbonate solution and then again with water, dried and evaporated. The residue is triturated with a 8:2 mixture of n-hexane and ether, and the separated solid is filtered off. The resulting protected pentapeptide, $R_f^{(3)}=0.72$, is dissolved in 10 ml of a 8 n hydrochloric acid solution in dioxane, the solution is allowed to stand for 15 minutes, and then the free pentapeptide hydrochloride is precipitated with dry ether. The resulting substance is dissolved in 20 ml of dimethyl formamide, the pH of the solution is adjusted to 8 with triethyl amine, and 2.6 g (6.8 mmoles) of Boc-Val-OPfp are added. The solution is stirred for one hour under maintaining the pH at the initial value, then the solvent is evaporated, the residue is dissolved in ethyl acetate, and the solution is washed as described above. The washed solution is dried and evaporated, and the residue is triturated with dry ether. The resulting protected hexapeptide, $R_f^{(3)}=0.83$, is filtered off, dissolved in 10 ml of a 8 n hydrochloric acid solution in dioxane, and after 15 minutes of standing the free hexapeptide hydrochloride, $R_f^{(5)}=0.65$, is precipitated with dry ether. This product is dissolved in 20 ml of dimethyl formamide, the pH of the solution is adjusted to 8 with triethyl amine, and 2.2 g (5 mmoles) of Boc-Arg(NO$_2$)-OPfp are added. The mixture is stirred for one hour under maintaining the pH at the initial value, thereafter it is diluted with 60 ml of chloroform, and the resulting mixture is washed successively with 10% aqueous citric acid solution, 1 n aqueous hydrochloric acid and water. The solution is dried, evaporated, and the residue is triturated with a 1:1 mixture of ethanol and ether. The resulting protected heptapeptide, $R_f^{(3)}=0.65$, is dissolved in 10 ml of a 8 n hydrochloric acid solution in dioxane, and after 15 minutes of standing the free heptapeptide hydrochloride, $R_f^{(5)}=0.40$, is precipitated with dry ether. The solid is filtered off, washed, dried and then dissolved in 15 ml of dimethyl formamide. The pH of the solution is adjusted to 8, and 1.8 g (5 mmoles) of Z-Sar-OPfp are added. The solution is stirred for 30 minutes under maintaining the pH at the initial value, then diluted with 45 ml of chloroform and shaken with water. The mixture is dried, evaporated, the residue is triturated with dry ether and the solid is filtered off. 2.12 g (29.6% calculated for His which corresponds to a yield of 82% in the individual steps) of Z-Sar-Arg(NO$_2$)-Val-Tyr(Bzl)-Ile-His(Dnp)-Pro-Lac-OBzl are obtained; $R_f(3) = 0.465$, m.p.: 204°–213° C.

Step 3

Removal of the protecting groups 2.3 ml (30 mmoles) of 2-mercaptoethanol are added to a solution of 1.45 g (1 mmole) of the protected octapeptide, prepared as described in Step 2, in 5 ml dimethyl formamide. After one hour of stirring dry ether is added to the mixture, the resulting protected octapeptide which is now free from the Dnp group is separated and purified by precipitation from methanol and ether. 1.14 g (89%) of the partially deprotected peptide are obtained; $R_f(4) = 0.60$. This substance is dissolved in 40 ml of a 5:1:2 mixture of methanol, acetic acid and water, 0.6 g of a 10% palladium-on-carbon catalyst are added, and the mixture is hydrogenated for 20 hours under vigorous stirring. Thereafter the catalyst is filtered off, washed with the above solvent mixture, and the filtrate is evaporated to dryness. 0.7 g (84%) of (Sar$^1$,Lac$^8$)-Ang-II are obtained.

Step 4

The crude peptide is purified according to the general method described above. The physical constants of the pure product are as follows: Chromatographic constants: $R_f(6) = 0.17$, $R_f(7) = 0.40$, $R_f(8) = 0.21$.

Amino acid analysis: Pro 1.0 (1), Val 1.0 (1), Ile 1.03 (1), Tyr 0.85 (1), His 0.85 (1), Arg 0.96 (1), Sar 1.0 (1).

EXAMPLE 2

Preparation of (sarcosine$^1$,ethyl L-Lactate$^8$)-angio-tensin-II

Step 1

Preparation of Boc-Pro-Lac-OEt 4.8 g (30 mmoles) of carbonyldiimidazole are added at 0° C., within 10 minutes, to a solution of 4.3 g (20 mmoles) of Boc-Pro-OH in 20 ml of dry tetrahydrofuran. Thereafter a cold solution of 2.1 g (20 mmoles) of ethyl L-lactate in tetrahydrofuran is added dropwise to the mixture at the same temperature. The mixture is stirred for additional 30 minutes at 0° C. and then for 2 hours at 20° C., and allowed to stand in a refrigerator overnight. Next day tetrahydrofuran is distilled off, the residue is dissolved in 40 ml of ethyl acetate, and the solution is washed successively with 1 n aqueous hydrochloric acid (2×15 ml), water, 5% aqueous sodium hydrocarbonate solution (twice) and then again with water. The solution is dried, the solvent is evaporated, and the oily residue is dried in a desiccator until constant weight. 2.22 g (36%) of Boc-Pro-Lac-OEt are obtained; $R_f(3) = 0.77$, $R_f(1) = 0.36$.

Step 2

Preparation of Z-Sar-Arg(NO$_2$)-Val-Tyr(Bzl)-Ile-His(Dnp)-Pro-Lac-OEt

A solution of 1.8 g (6 mmoles) of Boc-Pro-Lac-OEt in 8 ml of a 7.5 n hydrochloric acid solution in dioxane is allowed to stand for 15 minutes. 30 ml of ether are added to the solution, and the mixture is evaporated to dryness. The resulting free peptolide hydrochloride, $R_f(4) = 0.31$, is dissolved in 15 ml of dimethyl formamide, the pH of the solution is adjusted to 8 with triethyl amine and 2.9 g (5 mmoles) of Boc-His(Dnp)-OPfp are added. After one hour the solvent is replaced by ethyl acetate, and the resulting solution is washed successively with 10% aqueous citric acid solution, 1 n aqueous hydrochloric acid, 5% aqueous sodium hydrocarbonate solution and then again with water. The solution is dried, evaporated, and the resulting protected tripeptide, $R_f(2) = 0.69$, is dissolved immediately in 20 ml of a 7.5 n hydrochloric acid solution in dioxane. After 20 minutes of standing the free tripeptide hydrochloride, $R_f(4) = 0.19$, is precipitated with dry ether, the substance is dissolved in 15 ml of dimethyl formamide, the pH of the solution is adjusted to 8 with triethyl amine and 3.0 g (7.5 mmoles) of Boc-Ile-OPfp are added. The mixture is allowed to stand for 30 minutes under maintaining the pH at the initial value, thereafter the solvent is evaporated, the residue is dissolved in ethyl acetate, and the resulting solution is washed as described above. The solution is dried, evaporated, the residue is triturated with a 2:8 mixture of ether and n-hexane and the solid is filtered off. The resulting protected tetrapeptide, $R_f(3) = 0.36$, is dissolved in 10 ml of a 8 n hydrochloric acid solution in dioxane, and after 15 minutes of standing the free tetrapeptide hydrochloride, $R_f(5) = 0.27$, is precipitated with dry ether. The product is dissolved immediately in 20 ml of dimethyl formamide, the pH of the solution is adjusted to 8, and 3.24 g (6 mmoles) of Boc-Tyr(Bzl)-OPfp are added. The solution is allowed to stand for 30 minutes while the pH was maintained at the initial value, thereafter the solvent is evaporated and the residue is dissolved in ethyl acetate. 0.22 ml of N,N-dimethylamino-ethylamine are added to the solution, the mixture is allowed to stand for 10 minutes, then washed as described above, dried and evaporated. The residue is triturated with n-hexane and filtered. The resulting protected pentapeptide, $R_f(2) = 0.64$, is dissolved in 10 ml of a 8 n hydrochloric acid solution in dioxane, and after 15 minutes of standing the free pentapeptide hydrochloride, $R_f(4) = 0.33$, is precipitated with dry ether. The product is dissolved in 15 ml of dimethyl formamide, the pH of the solution is adjusted to 8 with triethyl amine, and 2.1 g (5.5 mmoles) of Boc-Val-OPfp are added. The solution is allowed to stand for 30 minutes under maintaining the pH at the initial value, then it is evaporated, the residue is dissolved in ethyl acetate, and this solution is washed as described above. The solution is dried, evaporated, the residue is triturated with n-hexane and then filtered. The resulting protected hexapeptide, $R_f(2) = 0.76$, is dissolved immediately in 10 ml of a 8 n hydrochloric acid solution in dioxane, and after 15 minutes of standing the free hexapeptide hydrochloride, $R_f(4) = 0.34$, is precipitated with dry ether. This substance is dissolved in 20 ml of dimethyl formamide, the pH of the solution is adjusted to 8, and 3.96 g (6 mmoles) of Boc-Arg(NO$_2$)-OPfp are added. The solution is allowed to stand for one hour under maintaining the pH at the initial value, then diluted with 60 ml of chloroform, washed as described above, dried and evaporated. The residue is triturated with dry ethanol and filtered. The resulting protected heptapeptide, $R_f(3) = 0.78$, is dissolved in 10 ml of a 8 n hydrochloric acid solution in dioxane, and after 15 minutes of standing the product is precipitated with dry ether. The resulting free heptapeptide hydrochloride, $R_f(4) = 0.56$, is dissolved immediately in 20 ml of dimethyl formamide, the pH of the solution is adjusted to 8, and 2.12 g (5.5 mmoles) of Z-Sar-OPfp are added. The solution is allowed to stand for 30 minutes under maintaining the pH at the initial value, then diluted with 60 ml of chloroform and washed as described above. The solution is dried, evaporated, the residue is triturated with ethanol, and the solid is recrystallized from ethanol. 1.21 g (17.5% calculated for His; this corresponds to a yield of 75% in the individual steps) of Z-Sar-Arg(NO$_2$)-Val-Tyr(Bzl)-Ile-His(Dnp)-Pro-Lac-OEt are obtained; m.p.: 208°–212° C., R$_f$(3)=0.5.

Step 3

Removal of the protecting groups 3 ml of 2-mercaptoethanol are added to a solution of 1.21 g (0.88 mmoles) of the protected octapeptide, prepared as described in Step 2, in 5 ml of dimethyl formamide. The mixture is stirred for one hour, then the product is precipitated with dry ether, filtered and washed. The solid is dissolved in methanol and precipitated again with dry ether. 0.94 g (89%) of the corresponding partially deprotected octapeptide, which is free of dinitrophenyl protecting group, are obtained; R$_f$(4)=0.59. This substance is dissolved in 20 ml of a 5:1:1 mixture of methanol, acetic acid and water, 0.5 g of a 10% palladium-on-carbon catalyst are added, and hydrogen is bubbled through the mixture for 20 hours under vigorous stirring. The progress of the reaction is monitored by thin layer chromatography. At the end of the reaction the catalyst is filtered off, washed with the above solvent mixture, the filtrate and the wash are combined and evaporated to dryness. The residue is triturated with a mixture of ethanol and ether and filtered. 0.72 g (96%) of (Sar$^1$,Lac-OEt$^8$)-Ang-II are obtained.

Step 4

The crude free peptide obtained in the above step is purified according to the general procedure described above. The pure peptide has the following physical constants: Chromatographic characteristics: R$_f$(6)=0.24, R$_f$(7)=0.53, R$_f$(8)=0.36. Amino acid analysis: Pro 1.02 (1), Val 0.97 (1), Ile 1.08 (1), Tyr 0.91 (1), His 1.00 (1), Arg 1.07 (1), Sar 1.0 (1).

EXAMPLE 3

Preparation of (sarcosine$^1$, L-2-hydroxy-3-methylvaleric acid$^8$)-angiotensin-II Step 1

Preparation of H-HMV-OBzl 20 ml of a 4 n hydrochloric acid solution in ethyl acetate are added to a suspension of 7.12 g (40 mmoles) of H-HMV-ONa in 10 ml of ethyl acetate. The mixture is stirred for 2 hours and then the pH of the mixture is adjusted to 3 with triethyl amine. The separated precipitate is filtered off and washed twice with 20 ml of ethyl acetate, each. The pH of the filtrate is adjusted to 6 with triethyl amine and then 8 ml (60 mmoles) of benzyl bromide and 8.4 ml (60 mmoles) of triethyl amine are added. The resulting mixture is refluxed for 8 hours, the separated inorganic salt is filtered off, and the filtrate is washed successively with water, 1 n aqueous hydrochloric acid, 5% aqueous sodium hydrocarbonate solution and then again with water. The solution is dried, evaporated, and the resulting 5.6 g (63%) of H-HMV-OBZl is purified by distillation in vacuo. The product boils at 134°–136° C./5 mm Hg; [α]$_D^{25}$=−13.9° (c=1%, in acetone).

Step 2

Preparation of Boc-Pro-HMV-OBzl 3.2 g (20 mmoles) of carbonyldiimidazole are added at 0° C., within 10 minutes, to a solution of 2.7 g (12.5 mmoles) of Boc-Pro-OH in 15 ml of dry tetrahydrofuran. A cold solution of 2.8 g (12.5 mmoles) of H-HMV-OBzl in 10 ml of tetrahydrofuran is added to the mixture at the same temperature, and the resulting mixture is stirred at 0° C. for 30 minutes and then at 20° C. for 2 hours. The mixture is allowed to stand in a refrigerator overnight. Next day tetrahydrofuran is evaporated, the residue is dissolved in 40 ml of ethyl acetate, and the solution is washed successively with 1 n aqueous hydrochloric acid (2×15 ml), water, 5% aqueous sodium hydrocarbonate solution and then again with water. The solution is dried, evaporated, and the oily residue is dried until constant weight at 25° C. 3.19 g (65%) of Boc-Pro-HMV-OBzl are obtained; R$_f$(2)=0.90, R$_f$(1)=0.33.

Step 3

Preparation of Z-Sar-Arg(NO$_2$)-Val-Tyr(Bzl)-Ile-His(Dnp)-Pro-HMV-OBzl 2.52 g (6 mmoles) of Boc-Pro-HMV-OBzl are dissolved in 8 ml of a 8 n hydrochloric acid solution in dioxane, the mixture is allowed to stand for 15 minutes, 30 ml of dry ether are added, and the mixture is evaporated to dryness. The free dipeptolide hydrochloride, R$_f$(4)=0.30, obtained as residue is dissolved in 15 ml of dimethyl formamide, the pH of the mixture is adjusted to 8 with triethyl amine, and 2.9 g (5 mmoles) of Boc-His-(Dnp)-OPfp are added. The solution is allowed to stand for one hour under maintaining the pH at the initial value, then evaporated, and the residue is dissolved in ethyl acetate. This solution is washed successively with 1 n aqueous hydrochloric acid, water and 5% aqueous sodium hydocarbonate solution, dried, evaporated, and the protected tripeptide, R$_f$(2)=0.67, obtained as residue in dissolved in 10 ml of a 8 n solution of hydrochloric acid in dioxane. After 20 minutes of standing the free tripeptide hydrochloride, R$_f$(4)=0.18, is precipitated with dry ether. This substance is dissolved in 15 ml of dimethyl formamide, the pH of the solution is adjusted to 8 with triethyl amine, and 2.4 g (6 mmoles) of Boc-Ile-OPfp are added. The solution is allowed to stand for one hour under maintaining the pH at the initial value, then evaporated, and the residue is dissolved in chloroform. This solution is washed successively with water, 1 n aqueous hydrochloric acid and 5% aqueous sodium hydrocarbonate solution, dried and evaporated. The protected tetrapeptide obtained as residue is triturated with n-hexane, n-hexane is decanted, the residue is triturated with dry ether and filtered. The resulting protected tetrapeptide, R$_f$(2)=0.65, is dissolved in 10 ml of a 8 n hydrochloric acid solution in dioxane, and after 15 minutes of standing the free tetrapeptide hydrochloride, R$_f$(4)=0.27, is precipitated with dry ether. This substance is dissolved in 15 ml of dimethyl formamide, the pH of the solution is adjusted to 8, and 2.96 g of Boc-Tyr(Bzl)-OPfp are added. The solution is allowed to stand for 30 minutes while maintaining the pH at the initial value and then evaporated. The residue is dissolved in ethyl acetate, 0.22 ml of N,N-dimethylamino-ethylamine are added to the solution, and after 10 minutes of standing the mixture is washed successively with 10% aqueous citric acid solution, 1 n aqueous hydrochloric acid and 5% aqueous sodium hydrocarbonate solution. The solution is dried, evaporated, the residue is triturated with n-hexane and then filtered. The resulting protected pentapeptide, $R_f^{(3)}=0.75$, is dissolved in 10 ml of a 8 n hydrochloric acid solution in dioxane, the solution is allowed to stand for 15 minutes, and then the free pentapeptide hydrochloride, $R_f^{(4)}=0.60$, is precipitated with dry ether. The resulting substance is dissolved immediately in 20 ml of dimethyl formamide, the pH of the solution is adjusted to 8, and 2.3 g (6 mmoles) of Boc-Val-OPfp are added. The resulting solution is allowed to stand for one hour under maintaining the pH at the initial value, then evaporated, the residue is dissolved in chloroform, and the chloroform solution is washed successively with 10% aqueous citric acid solution, 1 n aqueous hydrochloric acid, 5% aqueous sodium hydrocarbonate solution and water. The solution is dried, evaporated, the residue is triturated with n-hexane, and the protected hexapeptide, $R_f^{(3)}=0.71$, is filtered off. This substance is dissolved in 10 ml of a 8 n hydrochloric acid solution in dioxane, the solution is allowed to stand for 15 minutes, and then the free hexapeptide hydrochloride, $R_f^{(4)}=0.34$, is precipitated with dry ether. This substance is dissolved immediately in 20 ml of dimethyl formamide, the pH of the solution is adjusted to 8, and 2.64 g (6 mmoles) of Boc-Arg(NO$_2$)-OPfp are added. The solution is allowed to stand for one hour while maintaining the pH at the initial value and then evaporated. The residue is dissolved in chloroform, the solution is washed successively with 10% aqueous citric acid containing 10% of dimethyl formamide, 1 n aqueous hydrochloric acid, 5% aqueous sodium hydrocarbonate solution and water, dried and evaporated. The residue is triturated with a 8:2 mixture of ether and ethanol and filtered off. The resulting protected heptapeptide, $R_f^{(3)}=0.63$, is dissolved in 10 ml of a 8 n hydrochloric acid solution in dioxane, and after 15 minutes of standing the free heptapeptide hydrochloride, $R_f^{(5)}=0.45$, is preicipitated with dry ether. The product is filtered off, washed, dried, dissolved in 20 ml of dimethyl formamide, the pH of the solution is adjusted to 8, and 2.3 g (6 mmoles) of Z-Sar-OPfp are added. The solution is allowed to stand for 30 minutes under maintaining the pH at the initial value, then diluted with 60 ml of chloroform, washed with 1 n aqueous hydrochloric acid and water, dried and evaporated. The residue is triturated with a 8:2 mixture of ether and ethanol, the solid is filtered off and washed. 2.36 g (30% calculated for His which corresponds to a yield of 82% in the individual steps) of Z-Sar-Arg(NO$_2$)-Val-Tyr(Bzl)-Ile-His(Dnp)-Pro-HMV-OBzl are obtained; m.p.: 193°–202° C., $R_f^{(3)}=0.30$, $R_f^{(4)}=0.86$.

Step 4

Removal of the protecting groups 2.8 ml of 2-mercaptoethanol are added to a solution of 2.0 g (1.25 mmoles) of the protected octapeptide, prepared as described in Step 3, in 5 ml of dimethyl formamide. The mixture is stirred for one hour, thereafter the product is precipitated with dry ether, washed with ether, dissolved in methanol and precipitated again with ether. 1.44 g (80%) of the partially deprotected octapeptide, free of dinitrophenyl group, are obtained; $R_f^{(4)}=0.41$. This substance is dissolved in 30 ml of a 5:2:1 mixture of methanol, acetic acid and water, 0.7 g of a 10% palladium-on-carbon catalyst are added, and hydrogen is bubbled through the mixture for 20 hours under vigorous stirring. At the end of the reaction the catalyst is filtered off, washed with 20 ml of the above solvent mixture, the wash and the filtrate are combined and evaporated to dryness. The residue is triturated with a 1:1 mixture of ethanol and ether and then filtered. 0.65 g (67%) of (sarcosine$^1$, L-2-hydroxy-3-methylvaleric acid$^8$)-angiotensin-II are obtained.

Step 5

The crude product obtained as described in Step 4 is purified according to the general procedure described above. The pure product has the following physical constants: Chromatographic characteristics: $R_f^{(6)}=0.26$, $R_f^{(7)}=0.52$, $R_f^{(8)}=0.30$. Amino acid analysis: Pro 1.06 (1), Val 1.03 (1), Ile 1.03 (1), Tyr 0.65 (1), His 0.99 (1), Arg 0.95 (1), Sar 1.0 (1).

What we claim is:

1. An octapeptide of angiotensin-II antagonizing effects having the formula (I), X-Arg-Val-Tyr-Ile-His-Pro-Y-OA  (I)

wherein

X is sarcosyl,

Y is a residue of lactic acid or L-2-hydroxy-3-methylvaleric acid, and

A is hydrogen or a $C_{1-5}$ alkyl group, or a phamaceutically acceptable acid addition salt or complex thereof.

2. L-Sarcosyl-L-arginyl-L-valyl-L-tyrosyl-L-isoleucyl-L-histidyl-L-prolyl-L-2-hydroxy-3-methylvaleric acid or a lower alkyl ester thereof.

3. L-Sarcosyl-L-arginyl-L-valyl-L-tyrosyl-L-isoleucyl-L-histidyl-L-prolyl-L-lactic acid or a lower alkyl ester thereof.

4. A hypotensive composition containing as active ingredient a phramaceutically effective amount of an octapeptide of the formula (I), X-Arg-Val-Tyr-Ile-His-Pro-Y-OA  (I)

as defined in claim 1, or a pharamcetically acceptable acid addition salt or complex thereof and a pharmaceutical acceptable carrier.

5. A hypotensive method of treating a suscpetible animal subject which comprises administering an effective amount of an octapeptide as defined in claim 1 or a pharmaceutically effective acid-addition salt of complex thereof.

* * * * *